US009056879B2

(12) United States Patent
Li et al.

(10) Patent No.: US 9,056,879 B2
(45) Date of Patent: Jun. 16, 2015

(54) METHOD OF MANUFACTURING HYDROPHILIC SILICONE PREPOLYMER

(71) Applicant: Pegavision Corporation, Taoyuan County (TW)

(72) Inventors: Heng-Yi Li, Taoyuan County (TW); Wei-Jia Ting, Taoyuan County (TW); Yu-Chin Lai, Taoyuan County (TW); Han-Yi Chang, Taoyuan County (TW)

(73) Assignee: PEGAVISION CORPORATION (TW)

( * ) Notice: Subject to any disclaimer, the term of this patent is extended or adjusted under 35 U.S.C. 154(b) by 324 days.

(21) Appl. No.: 13/718,894

(22) Filed: Dec. 18, 2012

(65) Prior Publication Data

US 2013/0172592 A1  Jul. 4, 2013

(30) Foreign Application Priority Data

Dec. 29, 2011  (TW) .............................. 100149572 A

(51) Int. Cl.
| | | |
|---|---|---|
| C07F 7/10 | (2006.01) | |
| C07F 7/08 | (2006.01) | |
| C08G 18/61 | (2006.01) | |
| C08G 77/458 | (2006.01) | |
| G02B 1/04 | (2006.01) | |
| C08G 18/67 | (2006.01) | |
| C08G 18/75 | (2006.01) | |
| C08G 18/81 | (2006.01) | |

(52) U.S. Cl.
CPC ............. *C07F 7/0879* (2013.01); *C07F 7/0854* (2013.01); *C08G 18/61* (2013.01); *C08G 77/458* (2013.01); *G02B 1/043* (2013.01); *C08G 18/672* (2013.01); *C08G 18/755* (2013.01); *C08G 18/8116* (2013.01)

(58) Field of Classification Search
CPC ..................................................... C07F 7/0879
USPC ........................................................... 556/419
See application file for complete search history.

(56) References Cited

U.S. PATENT DOCUMENTS

| | | | |
|---|---|---|---|
| 4,136,250 A | 1/1979 | Mueller et al. | 528/29 |
| 4,259,467 A | 3/1981 | Keogh et al. | 526/279 |
| 4,260,725 A | 4/1981 | Keogh et al. | 526/279 |
| 5,516,869 A | 5/1996 | Lucarelli et al. | 528/15 |
| 6,503,632 B1 | 1/2003 | Hayashi et al. | 428/447 |
| 7,423,074 B2 | 9/2008 | Lai et al. | 523/106 |
| 7,632,876 B2 | 12/2009 | Lai et al. | 523/106 |
| 8,129,442 B2 | 3/2012 | Ueyama et al. | 523/107 |
| 2002/0016383 A1 | 2/2002 | Iwata et al. | 523/106 |
| 2006/0063852 A1 | 3/2006 | Iwata et al. | 523/106 |
| 2006/0142525 A1 | 6/2006 | Lai et al. | 528/25 |
| 2008/0231798 A1* | 9/2008 | Zhou et al. | 351/160 H |
| 2008/0293844 A1 | 11/2008 | Padsalgikar et al. | 523/113 |

FOREIGN PATENT DOCUMENTS

| | | | | |
|---|---|---|---|---|
| CN | 1409829 | 4/2003 | ............ | C08F 283/12 |
| CN | 101039982 | 9/2007 | .............. | A61L 27/16 |
| EP | 1 116 740 | 7/2001 | .............. | C08G 69/42 |
| JP | S5694324 | 7/1981 | ............ | C08F 283/12 |
| JP | 2001072739 | 3/2001 | .............. | A61L 27/00 |
| JP | 2008525615 | 7/2008 | ................ | A61F 2/16 |
| JP | 2008525617 | 7/2008 | ................ | A61F 2/14 |
| WO | WO2009099164 | 8/2009 | ................ | C08F 290/06 |

* cited by examiner

*Primary Examiner* — Porfirio Nazario Gonzalez
*Assistant Examiner* — Kofi Adzamli
(74) *Attorney, Agent, or Firm* — Hayes Soloway P.C.

(57) ABSTRACT

A method for manufacturing a hydrophilic silicone prepolymer is disclosed. The method comprises ring-opening polymerization (ROP) of cyclosiloxanes, hydrosilylation of polysiloxanes, copolymerization, and end-capping reaction. After the above processes, the hydrophilic silicone prepolymer can be obtained.

13 Claims, No Drawings

METHOD OF MANUFACTURING HYDROPHILIC SILICONE PREPOLYMER

RELATED APPLICATIONS

This application claims priority to Taiwan Application Serial Number 100149572 filed Dec. 29, 2011, which is herein incorporated by reference.

BACKGROUND

1. Technical Field

The present disclosure relates to a material for contact lenses, and more particularly, to a method for manufacturing a hydrophilic silicone prepolymer for making contact lenses.

2. Description of Related Art

Traditional contact lenses may result in corneal hypoxia due to the lack of oxygen and are not suitable for a prolonged wearing. At present, silicone hydrogel lenses in the market all declare having high oxygen permeability. Since the contact lens made of silicone hydrogel allows sufficient oxygen directly through the lenses to the cornea, silicone hydrogel has become one of the preferable classes of contact lenses.

However, since silicone hydrogel is mainly composed of silicone, which is hydrophobic in nature, silicone hydrogel is still causing corneal relatively dehydrated, dry and irritated. In this regard, how to keep the silicone hydrogel lens moisturizing is the most challenging issue in the industry. There are some methods which keep silicone hydrogel lens moisture comprising: performing a surface treatment of the silicone-rich hydrophobic lenses by a plasma process, adding polyvinylpyrrolidone into the silicone hydrogel formulation and using a silicone prepolymer having a polyoxyethylene side chain.

Silicone hydrogel lenses are typically made from one or two kinds of silicone monomer, polymer or prepolymer, and these silicone components are hydrophobic. Silicone monomers typically have molecular weights less than 500 and with up to 4 silicon atoms in their structure, for example, 3-(methacryloyloxypropyl)-tris(trimethylsiloxy)silane (TRIS). Silicone macromers usually have a number average molecular weight of about 500 to 1,100, and these macromers have linear multiple siloxane units and single ethylenically unsaturated group. Silicone prepolymers have at least two ethylenically unsaturated groups and have repeating units of linear multiple siloxanes. Although Keogh et al. in 1981 disclosed some structures of these silicone macromer or prepolymer (U.S. Pat. No. 4,259,467), only the hydrophilic silicone prepolymer having a polyoxyethylene side chain was synthesized and used in the manufacture of silicone hydrogel lenses. (U.S. Patent Application Publication 2006/0063852). No manufacturing methods for other hydrophilic group-containing hydrophilic silicone prepolymers have ever been proposed.

SUMMARY

Therefore, one of the purposes of the present disclosure is to provide a manufacturing method of a hydrophilic silicone prepolymer. The manufacturing method comprises a ring-opening polymerization of cyclic siloxanes, a hydrosilylation of polysiloxanes, a copolymerization and a end-capping reaction. By the above reactions, it gives the hydrophilic silicone prepolymer.

Firstly, it is performing the ring-opening polymerization of cyclic siloxanes. A cyclic siloxane and a cyclic hydrogen siloxane are catalyzed by a strong acid, and then inserted into a hydroxyl-terminated disiloxane, so as to form a hydroxyl-terminated polysiloxane containing multi Si—H groups.

Secondly, it is performing the hydrosilylation of the hydroxyl-terminated polysiloxane containing multi Si—H groups. A carbon-carbon double bond of a hydrophilic monomer is added to the Si—H groups of the polysiloxane by a rhodium-based catalyst, and then the hydrophilic monomer is connected to the polysiloxane to form a hydroxyl-terminated silicone diol containing a hydrophilic side-chain, in which the hydrophilic monomer is an amide-containing hydrophilic monomer or a phosphorylcholine-containing hydrophilic monomer.

Thirdly, it is performing a copolymerization. The silicone diol produced (p mole) under the hydrosilation is polymerized with a diisocyanate (q mole) in a different molar ratio by a catalyst of dibutyltin dilaurate (DBTDL), so as to form a diol copolymer end-capped with hydroxyl groups as p>q or form an isocyanate copolymer end-capped with isocyanate groups as p<q.

Finally, it is performing an end-capping reaction. In one hand, the diol copolymer is end-capped with an ethylenically unsaturated monomer containing electrophiles, so as to give a hydrophilic silicone prepolymer end-capped with ethylenically unsaturated groups. On the other hand, the isocyanate copolymer is end-capped with an ethylenically unsaturated monomer containing nucleophiles, so as to give a hydrophilic silicone prepolymer end-capped with ethylenically unsaturated groups.

According to one embodiment of the present disclosure, the cyclic siloxane is octamethylcyclotetrasiloxane (D4), and the cyclic hydrogen siloxane is 1,3,5,7-tetramethylcyclotetrasiloxane (D4h).

According to one embodiment of the present disclosure, the disiloxane is 1,3-bis[3-(2-hydroxyethoxy)propyl]tetramethyl disiloxane or 1,3-bis[hydroxybutyl]tetramethyl disiloxane.

According to one embodiment of the present disclosure, the amide-containing hydrophilic monomer is selected from the group comprising N-vinyl pyrrolidone, N-allyl pyrrolidone, N-vinyl-N-methyl acetamide and a combination thereof.

According to one embodiment of the present disclosure, the phosphorylcholine-containing hydrophilic monomer is 2-methacryloyloxyethyl phosphorylcholine (MPG).

According to one embodiment of the present disclosure, the rhodium-based catalyst is tris(dibutylsulfide) rhodium trichloride.

According to one embodiment of the present disclosure, the diisocyanate is isophorne diisocyanate (IPDI), toluene-2,4-diisocyanate, or toluene-2,6-diisocyanate.

According to one embodiment of the present disclosure, the ethylenically unsaturated monomer containing electrophiles is selected from the group comprising isocyanatoethyl methacrylate, methacryloyl chloride and methacrylic anhydride.

According to one embodiment of the present disclosure, the ethylenically unsaturated monomer containing nucleophiles is 2-hydroxyethyl methacrylate (HEMA).

The other one of the purposes of the present disclosure is to provide a hydrophilic silicone prepolymer made by the methods. The hydrophilic silicone prepolymer has a structure of formula (I):

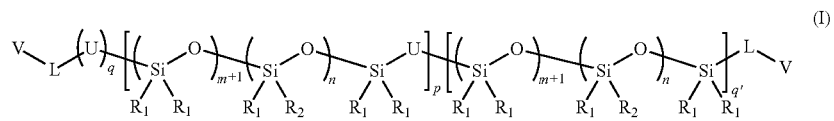

(I)

Wherein V is an ethylenically unsaturated group comprising acrylate, methacrylate, acrylamide, or methacrylamide. L is an C1-C12 linker connected between V and the diol copolymer or the diisocyanate copolymer, and comprises ester bond, ether bond or urethane linkage. U is a linker formed by the diisocyanate inserted into the hydrophilic silicone prepolymer. $R_1$ is a C1-C12 alkyl group or substituent. $R_2$ is the hydrophilic side chain containing the amide bond or the phosphorylcholine group. p is an integer from 0 to 5, m and n are integers from 1 to 70, and q and q' are 0 or 1, and $q+q'=1$.

According to one embodiment of the present disclosure, the molecular weight of the hydrophilic silicone prepolymer is less than 20,000 or preferred in a range of 5,000 to 20,000.

According to one embodiment of the present disclosure, the weight percentage of the hydrophilic side chain in the prepolymer is in a range of 5 wt % to 90 wt %.

According to one embodiment of the present disclosure, the hydrophilic silicone prepolymer is comprised in a polymeric material.

According to one embodiment of the present disclosure, the hydrophilic silicone prepolymer is comprised in a silicone hydrogel lens.

DETAILED DESCRIPTION

The following is described in detail to clearly illustrate the present disclosure. After understanding the embodiments of the present disclosure, the person in the art, however, may change and modify from the demonstration of the present disclosure, and the results of which is not departing from the present disclosure.

According to the above, it is to provide a manufacturing method of a hydrophilic silicone prepolymer. The manufacturing method comprises a ring-opening polymerization of cyclic siloxanes, a hydrosilylation of polysiloxanes, a copolymerization and an end-capping reaction. By the above reactions, it gives the hydrophilic silicone prepolymer.

Ring-Opening Polymerization of Cyclic Siloxanes

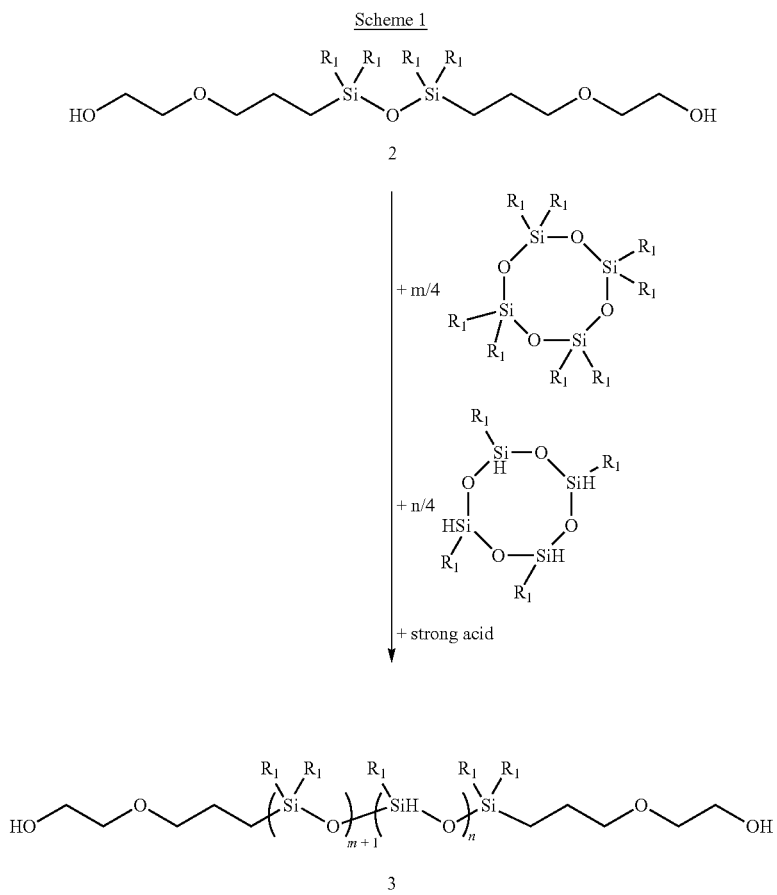

In the ring-opening polymerization (see Scheme 1), catalyzed by a strong acid, the cyclic siloxane and the cyclic hydrogen siloxane is ring opened at room temperature, and then inserted into a hydroxyl-terminated disiloxane (2), so as to form a hydroxyl-terminated polysiloxane containing multi Si—H groups (3). In which, the strong acid is trifluoromethanesulfonic acid (triflic acid, TFA) or sulfuric acid. And in the structure of the polysiloxane (3), $R_1$ is C1-C12 alkyl groups or substituents, and m and n are an integer of 1-70. It is worth noting, after the ring-opening and insertion of the cyclic hydrogen siloxane, the formed polysiloxane (3) can be performed in the following hydrosilylation.

According to one embodiment of the present disclosure, the cyclic siloxane is octamethylcyclotetrasiloxane (D4), and the cyclic hydrogen siloxane is 1,3,5,7-tetramethylcyclotetrasiloxane (D4h).

According to one embodiment of the present disclosure, the disiloxane is 1,3-bis[3-(2-hydroxyethoxy)propyl]tetramethyl disiloxane or 1,3-bis[hydroxybutyl]tetramethyl disiloxane.

is catalyzed by a rhodium-based catalyst and the reaction is performed at a temperature between 40° C. to 150° C. The absorption peaks of the Si—H bonds in the infrared spectrum 2127 cm$^{-1}$ and the vinyl bond in the infrared spectrum 1620 cm$^{-1}$ disappear as reaction goes completion and this can be used to follow the progress of hydrosilylation. In which, $R_2$ of the silicone diol (4) is the hydrophilic side chain having an amide bond or a phosphorylcholine group, and W represents a functional group having the amide bond or phosphorylcholine, so that the original hydrophobic silicone is converted into hydrophilic. Subsequently, the silicone diol (4) is copolymerized with a diisocyanate.

According to one embodiment of the present disclosure, the rhodium-based catalyst is tris(dibutylsulfide) rhodium trichloride.

According to one embodiment of the present disclosure, the amide-containing hydrophilic monomer is selected from the group comprising N-vinyl pyrrolidone, N-allyl pyrrolidone, N-vinyl-N-methyl acetamide and a combination thereof.

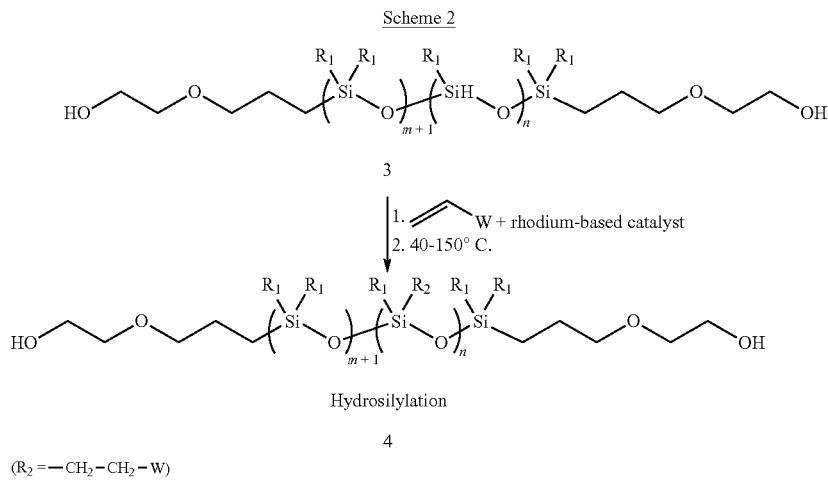

Scheme 2

In a hydrosilylation (see Scheme 2), a carbon-carbon double bond (C=C) of a hydrophilic monomer is added to Si—H bonds of a polysiloxane (3) by a rhodium-based catalyst, and then the hydrophilic monomer is connected to the polysiloxane (3) to form a hydroxyl-terminated silicone diol containing a hydrophilic side chain (4). This hydrosilylation According to one embodiment of the present disclosure, the phosphorylcholine-containing hydrophilic monomer is 2-methacryloyloxyethyl phosphorylcholine (MPC).

Copolymerization

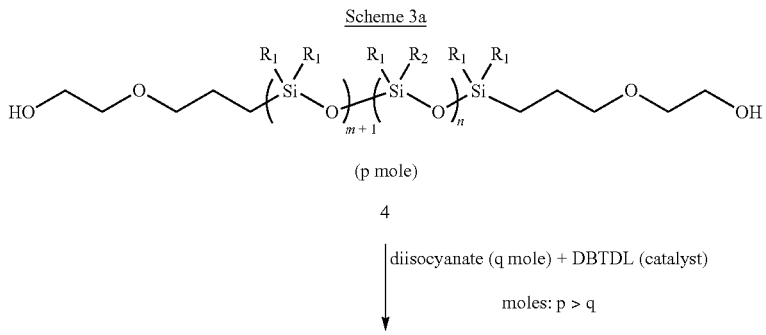

Scheme 3a

-continued

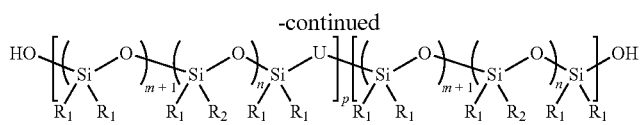

5

In the copolymerization (see Scheme 3a and 3b), a hydroxyl group of the silicone diol is copolymerized with a diisocyanate group of the diisocyanate by a catalyst of dibutyltin dilaurate (DBTDL), so as to form an amide ester bond. In Scheme 3a, when the moles of the silicone diol (4) (p mole) is larger than the moles of the diisocyanates (q mole), a diol copolymer end-capped with hydroxyl groups (5) may be formed. And the absorption peaks of the isocyanate bond in the infrared spectrum 2260 cm$^{-1}$ disappeared, in order to track the end point of the copolymerization. The U of the diol copolymer (5) is a linker formed by the reaction of the diisocyanate and silicone diol (4), in which the linker is

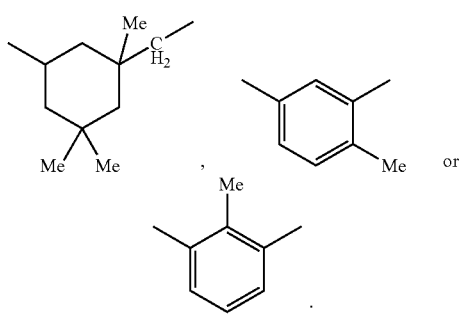

And p is an integer from 0 to 5.

(6) may be formed. And the absorption peaks of the hydroxyl bond in the infrared spectrum 3640 cm$^{-1}$ disappeared, in order to track the end point of the copolymerization. The U of the diisocyanate copolymer (6) is a linker formed by the reaction of the diisocyanate and silicone diol (4), in which the linker is

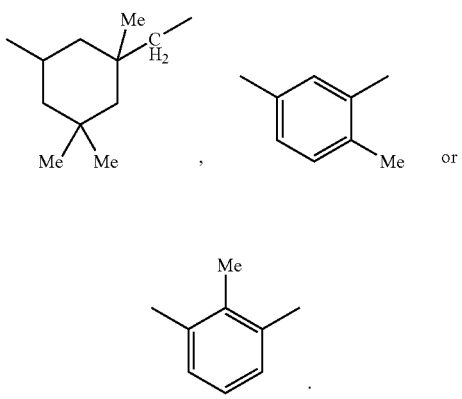

And p is an integer from 0 to 5.

According to one embodiment of the present disclosure, the diisocyanate is isophorne diisocyanate (IPDI), toluene-2,4-diisocyanate, or toluene-2,6-diisocyanate.

Scheme 3b

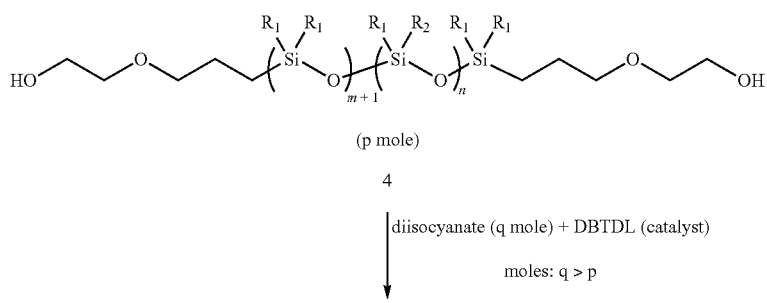

In Scheme 3b, when the moles of the silicone diol (4) (p mole) is less than the moles of the diisocyanates (q mole), a diisocyanate copolymer end-capped with isocyanate groups The diol copolymer (5) of Scheme 3a or the diisocyanate copolymer (6) of Scheme 3b may be end-capped respectively with ethylenically unsaturated monomers.

End-Capping Reaction of Diol Copolymer

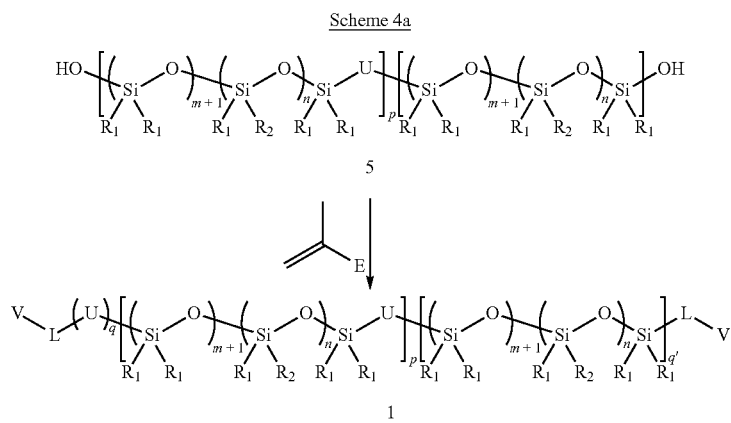

In the end-capping reaction of the diol copolymer (see Scheme 4a), the diol copolymer (5) is end-capped with an ethylenically unsaturated monomer containing electrophiles (E), so as to give a hydrophilic silicone prepolymer (1) end-capped with ethylenically unsaturated groups (V) and linker (L). The electrophiles (E) is ethyl isocyanate group (—NH-COOEt), halogen group (such as —Cl) or methacrylic group (—OOC—C(CH3)=CH2).

In this case, the V of the hydrophilic silicone prepolymer (1) is ethylenically unsaturated group, which contains acrylic group, methacrylic group, acrylamide or methyl acrylamide group. And L is C1-C12 linker connected between V and the diol copolymer (5), and contains ester bond, ether bond, or urethane bond. q is 0, and q' is 1.

According to one embodiment of the present disclosure, the ethylenically unsaturated monomer containing electrophiles (E) is selected from the group comprising isocyanatoethyl methacrylate, methacryloyl chloride and methacrylic anhydride.

End-Capping Reaction of Diisocyanate Copolymer

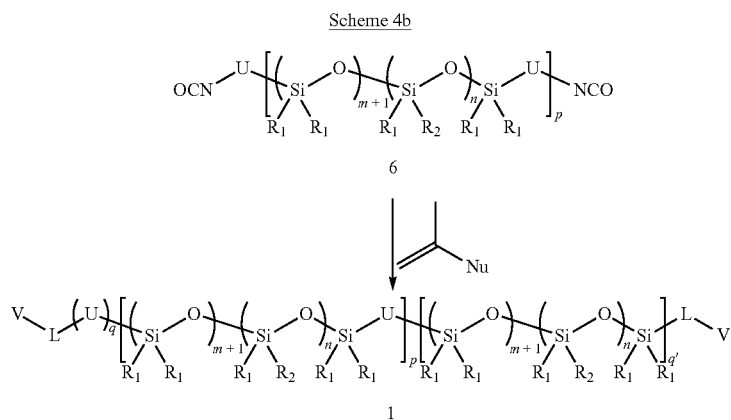

In the end-capping reaction of the diisocyanate copolymer (see Scheme 4b), the diisocyanate copolymer (6) is end-capped with an ethylenically unsaturated monomer containing nucleophiles (Nu), so as to give a hydrophilic silicone prepolymer (1) end-capped with ethylenically unsaturated groups (V) and linker (L). The nucleophiles (Nu) is hydroxy group.

In this case, the V of the hydrophilic silicone prepolymer (1) is ethylenically unsaturated group, which contains acrylic group, methacrylic group, acrylamide or methyl acrylamide group. And L is C1-C12 linker connected between V and the diisocyanate copolymer (6), and contains urethane bond. q is 1, and q' is 0.

According to one embodiment of the present disclosure, the ethylenically unsaturated monomer containing nucleophiles (Nu) is 2-hydroxyethyl methacrylate (HEMA).

According to one embodiment of the present disclosure, the Scheme 4a and 4b are shown the general formula of the hydrophilic silicone prepolymer (1), in which q and q' are 0 or 1, and q+q'=1.

According to one embodiment of the present disclosure, the molecular weight of the hydrophilic silicone prepolymer is less than 20000 or preferred in a range of 5000 to 20000.

According to one embodiment of the present disclosure, the weight percentage of the hydrophilic side chain in the prepolymer is in a range of 5 wt % to 90 wt %.

Example 1

Preparation of Prepolymer (1) Having Amide Side Chain

Preparation of 1,3-bis(3-(2-hydroxyethoxy)propyl)tetramethyl disiloxane 1,3-bis[3-(2-hydroxy-ethyleneoxy)propyl]tetramethyl siloxane is a known compound, i.e., the siloxane (2) in Scheme 1. Due to poor availability in the market, herein is provided a preparation of a starting material of making this compound.

31 g (more than 20 wt %) of ethylene glycol monoallyl ether and 25 mg of platinum divinyltetramethyldisiloxane complex were placed in an anaerobic vessel, stirred and heated to 65° C. 16.75 g of tetramethyldisiloxane was slowly added into the reaction mixture. And the absorption peaks of the Si—H bonds in the infrared spectrum 2127 $cm^{-1}$ were disappeared, so as to track the end point of the reaction.

After the reaction completed, ether and water (volume ratio 1:1) were added for extraction. The ether portion was collected and re-extracted for 2 to 3 times, and then magnesium sulfate was added to remove water and be filtered. After removing the ether, 21.5 g of 1,3-bis[3-(2-hydroxy-ethyleneoxy)propyl]tetramethyl siloxane was obtained.

Ring-Opening Polymerization of Cyclic Siloxane

Next, after octamethylcyclotetrasiloxane and 1,3,5,7-tetramethylcyclotetrasiloxane were ring-opened, they were polymerized with 1,3-bis(3-(2-hydroxy-ethyleneoxy)propyl)tetramethyl siloxane.

222 g (0.75 mole) of octamethylcyclotetrasiloxane, 19.2 g (0.080 mole) of 1,3,5,7-tetramethylcyclotetrasiloxane, 9.8 g (0.020 mole) of 1,3-bis(3-(2-hydroxy-ethyleneoxy)propyl) tetramethyl siloxane and 2.0 mg of trifluoromethanesulfonic acid (TFA) were mixed in an anaerobic vessel, and stirred at 25° C. for 24 hours. In the reaction mixture, 200 ml of diethyl ether and 350 ml of distilled water were added for extraction and the reaction solution was extracted with distilled water for several times, until the pH value of the ether portion becomes neutral, and the ether portion was collected. After ether was removed, the given crude product was added with 250 ml of methanol and 83 ml of distilled water, and stirred for 30 minutes. This process was repeated three times to give the purified product. It was then added with 130 ml of diethyl ether and magnesium sulfate to remove water; and then filtered. After ether was removed at low pressure, it gave a hydroxyl-terminated polysiloxane containing multi Si—H groups (239 g), which was a transparent viscous liquid.

Hydrosilylation of Amide Side Chain

Then, N-vinyl pyrrolidone was reacted with Si—H groups of the given polysiloxane, and then connected a hydrophilic side chain in the polysiloxane.

9.888 g of N-vinyl pyrrolidone was dissolved in 75 ml of toluene, and stirred at 100° C. for 1.5 hours. Next, slowly added 0.175 g of tris(dibutylsulfide) rhodium trichloride and 70 g of the polysiloxane, and keep stirring and heating. And the absorption peaks of the Si—H bonds in the infrared spectrum 2127 $cm^{-1}$ and the vinyl bond in the infrared spectrum 1620 $cm^{-1}$ disappeared which indicated the hydrosilylation was complete.

After the hydrosilylation was completed, the reaction mixture was cooled and toluene was removed at low pressure, and a methanol aqueous solution (methanol to water volume ratio=4:1) was used to purify the product twice. The product was then dissolved in dichloromethane, and added with magnesium sulfate to remove water and the solution was then filtered. After removing dichloromethane, it gives a hydroxyl-terminated silicone diol containing an amide side chain (A) (44.45 g, 56% of yield), which was a transparent viscous liquid.

Copolymerization

Then, the excess isophorne diisocyanate was copolymerized with the silicone diol (A), i.e. the above Scheme 3b.

43 g of the silicone diol (A), 1.75 g of isophorone diisocyanate (IPDI) and 0.134 g of dibutyltin dilaurate (DBTDL) were dissolved in dichloromethane, and stirred at reflux. When the absorption peak of the isocyanate bonds in the infrared spectrum 2127 $cm^{-1}$ turned into half, it gave an isocyanate copolymer end-capped with isocyanate groups. Then the reaction solution was cooled, but not to be purified, to be performed a one-pot reaction directly.

End-Capping Reaction

Then, 2-hydroxyethyl methacrylate (HEMA) was performed an end-capping reaction, i.e., the above Scheme 4b.

To add 0.9895 g of 2-hydroxyethyl methacrylate (HEMA) and 5.0 mg of methylhydroquinone into an unpurified diisocyanate copolymer, and was directly performed end-capping reaction. And the absorption peak of the isocyanate bonds in the infrared spectrum 2260 $cm^{-1}$ disappeared, the reaction was completed, the then dichloromethane was removed at low pressure to give 45 g of a prepolymer (1) having amide side chain.

Example 2

Preparation of Prepolymer (2) Having Amide Side Chain

In Example 2, the prepolymer (1) having amide side chain given by Example 1 was directly subject to an end-capping reaction with isocyanatoethyl methacrylate. The reaction steps of Example 2 before the end-capping reaction was the same as that in Example 1, including preparation of 1,3-bis (3-(2-hydroxyethoxy)propyl)tetramethyl disiloxane, ring-opening polymerization of cyclic siloxane, and hydrosilylation, so is not repeated here.

42 g of the silicone diol (A), 2.625 g of isocyanatoethyl methacrylate, 0.130 g of dibutyltin dilaurate (DBTDL), and 0.0043 g of methylhydroquinone were dissolved in dichloromethane, and stirred at reflux. Followed by the addition of 3 ml of methanol and then stirred for 2 hours. After the time was up, the dichloromethane was removed at low pressure, and purified by methanol aqueous solution (methanol to water volume ratio of 3:1) wash twice, to give 37.8 g of a prepolymer (2) having amide side chain.

Example 3

Preparation of Prepolymer (3) Having Amide Side Chain

Example 3 repeated the preparation of prepolymer (2) having amide side chain as that in Example 2. In Example 3, the unpurified silicon diol (A) given by the hydrosilylation of Example 1 was directly subject to an end-capping reaction with isocyanatoethyl methacrylate after removing toluene. The reaction steps of Example 3 before the end-capping reaction was the same as that of Example 1, including preparation of 1,3-bis[3-(2-hydroxyethoxy)propyl]tetramethyl disiloxane, ring-opening polymerization of cyclic siloxane, and hydrosilylation, so it is not repeated here.

127.5 g of the unpurified silicone diol (A), 7.09 g of isocyanatoethyl methacrylate, 0.404 g of dibutyltin dilaurate (DBTDL), and 0.013 g of O-methyl hydroquinone were dissolved in dichloromethane, and stirred for 60 hours. Followed by the addition of 2.924 g of methanol and then stirred for 2 hours. After the time was up, dichloromethane was removed at low pressure to give 131.3 g of a prepolymer (3) having amide side chain.

Compared to Example 2, in Example 3 only the solvent was removed in the hydrosilylation, and the purification step was omitted, directly performing the end-capping reaction. By the one-pot reaction, Example 3 significantly reduced the materials cost and saving time needed by the purification step. In view of manufacturing cost, the improved method has obvious advantages for the high cost of making the silicon hydrogel lenses.

Example 4

Preparation of Prepolymer Having Phosphorylcholine Side Chain

In Example 4, the polysiloxane given by the ring-opening reaction in Example 1 was subject to a hydrosilylation with 2-methacryloyloxyethyl phosphorylcholine (MPC), to give a hydroxyl-terminated silicone diol containing a phosphorylcholine side chain (B). The reaction steps of Example 4 before the hydrosilylation was the same as that in Example 1, including preparation of 1,3-bis(3-(2-hydroxyethoxy)propyl)tetramethyl disiloxane, and ring-opening polymerization, is not repeated here.

67 g of polysiloxane, 25 g of 2-methacryloyloxyethyl phosphorylcholine (MPC) and 0.00204 g/ml of tris(dibutylsulfide) rhodium trichloride were dissolved in toluene, and kept stirring and heating. When the absorption peaks of the Si—H bonds in the infrared spectrum 2127 cm$^{-1}$ and the vinyl bond in the infrared spectrum 1620 cm$^{-1}$ disappeared, the hydrosilylation was complete.

The reaction mixture was cooled and toluene was removed at low pressure. The silicone diol (B), 2.625 g of isocyanatoethyl methacrylate, 0.130 g of dibutyltin dilaurate (DBTDL), and 0.0013 g of O-methyl hydroquinone were dissolved in dichloromethane, and stirred for 60 hours. When the absorption peak of the isocyanate bonds in the infrared spectrum 2127 cm$^{-1}$ dropped in half, it gives an isocyanate copolymer end-capped with isocyanate groups. After the time was up, the dichloromethane was removed at low pressure, and product was purified by methanol aqueous solution (methanol to water volume ratio of 3:1) wash twice, and a prepolymer having phosphorylcholine side chain was obtained.

Preparation of Silicone Hydrogel Lenses

Example 5a 50 g of the prepolymer of Example 2, 15 g of 3-(methacryloyloxypropyl)-tris(trimethylsiloxy) silane (TRIS), 30 g of N-vinyl pyrrolidone (NVP), 5 g of 2-hydroxyethyl methacrylate (HEMA), 1 g of azo bis isobutyl nitrile (AIBN), and 0.1 g of triallylisocyanurate (TAIC) were dissolved in 10 g of t-amyl alcohol, for the preparation of a reaction solution. The reaction mixture was filtered through a 0.5 micron of filter, and then the mixture was filled into a polypropylene mold, and thermally cured at 70° C. for 2 hours to form a silicon hydrogel lens A. The lens A was extracted by 100 V % of isopropanol for 4 hours, to remove the extractables. Next, the lens A was extracted by 75 V % of isopropanol aqueous solution, 25 V % of isopropanol aqueous solution and then washed with distilled water, for 30 minutes, in order to reduce the isopropanol content within the silicone hydrogel lens A. Finally, the lens A was placed in the blister packs, which contains buffered saline solution and then sterilized at 121° C. for 30 minutes. The water content of the silicone hydrogel lens A was 42.6 wt %.

Examples 5b-5m

As the reactants and manufacturing method of Example 5a, and according to the recipes of Examples 5b-5m to prepare the silicone hydrogel lens B to M, wherein the solvents with high boiling point of Examples 5h to 5m were changed from t-amyl alcohol to nonanol. The silicone hydrogel prepolymer used in Examples 5b-5m was made by the method of Example 3. The recipes of Examples 5b to 5m (Table 1), and the water contents and extractable-isopropanol contents of the silicone hydrogel lens B to M (Table 2) are shown, respectively, as the following:

TABLE 1

| | Example | | | | | | | | | | | |
|---|---|---|---|---|---|---|---|---|---|---|---|---|
| | 5b | 5c | 5d | 5e | 5f | 5g | 5h | 5i | 5j | 5k | 5l | 5m |
| Prepolymer (g) | 50 | 50 | 50 | 50 | 55 | 55 | 50 | 50 | 50 | 50 | 55 | 55 |
| TRIS (g) | 15 | 15 | 15 | 15 | 10 | 10 | 15 | 15 | 15 | 15 | 10 | 10 |
| NVP (g) | 30 | 30 | 33 | 33 | 33 | 33 | 30 | 30 | 33 | 33 | 33 | 33 |
| HEMA (g) | 5 | 5 | 2 | 2 | 2 | 2 | 5 | 5 | 2 | 2 | 2 | 2 |
| TAIC (g) | 0.1 | 0.3 | 0.1 | 0.3 | 0.1 | 0.3 | 0.1 | 0.3 | 0.1 | 0.3 | 0.1 | 0.3 |
| t-amyl alcohol (g) | 10 | 10 | 10 | 10 | 10 | 10 | — | — | — | — | — | — |
| Nonanol (g) | — | — | — | — | — | — | 10 | 10 | 10 | 10 | 10 | 10 |
| AIBN (g) | 1 | 1 | 1 | 1 | 1 | 1 | 1 | 1 | 1 | 1 | 1 | 1 |

TABLE 2*

| | Silicone hydrogel lens | | | | | | | | | | | |
|---|---|---|---|---|---|---|---|---|---|---|---|---|
| | b | c | d | e | f | g | h | i | j | k | l | m |
| Extractable isopropanol content (wt %) | 15.3 | 13.9 | 15.4 | 11.2 | 17 | 14.8 | 19 | 18.1 | 20.1 | 18.1 | 17.1 | 24.4 |

TABLE 2*-continued

| | Silicone hydrogel lens | | | | | | | | | | |
|---|---|---|---|---|---|---|---|---|---|---|---|
| | b | c | d | e | f | g | h | i | j | k | l | m |
| water content (wt %) | 48.3 | 44 | 51.6 | 48.1 | 54 | 50.2 | 49.1 | 44.2 | 51.6 | 47.2 | 53.4 | 49.6 |

*The silicone hydrogel prepolymer shown in Table 2 was made by the method of Example 3.

The data of Table 2 are shown that, the silicone hydrogel lens B to M was made from the recipes of Examples 5b to 5m, and the water contents of which are in a range of 40 wt % to 55 wt %.

The preferred embodiments and examples of the present disclosure have been disclosed above. However, the manufacturing methods described above are not limited to the embodiment of the present disclosure. The person in the art can modify or transform variously without departing from the spirit and the scope of the present disclosure. Therefore, the protecting scope of the present disclosure should be defined as the following claims.

What is claimed is:

1. A hydrophilic silicone prepolymer, wherein a structure of the hydrophilic silicone prepolymer is shown as formula (I):

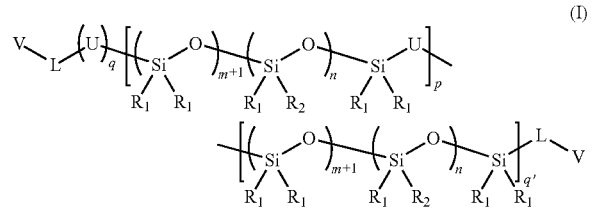

wherein V is an ethylenically unsaturated group comprising acrylate, methacrylate, acrylamide, or methacrylamide;

L is an C1-C12 linker connected between V and the diol copolymer or the diisocyanate copolymer, and comprises ester bond, ether bond or urethane linkage;

U is a linker formed by the diisocyanate inserted into the hydrophilic silicone prepolymer;

$R_1$ is a C1-C12 alkyl group or substituent;

$R_2$ is the hydrophilic side chain containing the amide bond or the phosphorylcholine group;

p is an integer from 0 to 5;

m and n are integers from 1 to 70; and q and q' are 0 or 1, and q+q'=1.

2. The hydrophilic silicone prepolymer of claim 1, wherein the molecular weight of the hydrophilic silicone prepolymer is less than 20000.

3. The hydrophilic silicone prepolymer of claim 1, wherein the weight percentage of the siloxane units with hydrophilic side chain in the prepolymer is in a range of 5 wt % to 90 wt % of the prepolymer.

4. The hydrophilic silicone prepolymer of claim 1, wherein the hydrophilic silicone prepolymer is comprised in a polymeric material.

5. The hydrophilic silicone prepolymer of claim 1, wherein the hydrophilic silicone prepolymer is comprised in a silicone hydrogel lens.

6. The hydrophilic silicone prepolymer of claim 2, wherein the molecular weight of the hydrophilic silicone prepolymer is in a range of 5000 to 20000.

7. A method for manufacturing a hydrophilic silicone prepolymer, comprising the steps of:

performing a ring-opening polymerization, wherein a cyclic siloxane and a cyclic hydrogen siloxane are catalyzed by a strong acid, and then inserted into a hydroxyl-terminated disiloxane, so as to form a hydroxyl-terminated polysiloxane containing multi silicon-hydrogen (Si—H) groups;

performing a hydrosilation, wherein a carbon-carbon double bond of a hydrophilic monomer is added to the Si—H groups of the polysiloxane by a rhodium-based catalyst, and then the hydrophilic monomer is connected to the polysiloxane to form a hydroxyl-terminated silicone diol containing a hydrophilic side-chain, in which the hydrophilic monomer is an amide-containing hydrophilic monomer or a phosphorylcholine-containing hydrophilic monomer;

performing a copolymerization, wherein p mole of the silicone diol produced under the hydrosilation is polymerized with q mole of a diisocyanate in a different molar ratio by a catalyst of dibutyltin dilaurate (DBTDL), so as to form a diol copolymer end-capped with hydroxyl groups as p>q or form an isocyanate copolymer end-capped with isocyanate groups as p<q; and performing a end-capping reaction, wherein the diol copolymer is end-capped with an ethylenically unsaturated monomer containing electrophiles or the isocyanate copolymer is end-capped with an ethylenically unsaturated monomer containing nucleophiles, so as to give the hydrophilic silicone prepolymer end-capped with ethylenically unsaturated groups.

8. The method of claim 7, wherein the cyclic siloxane is octamethylcyclotetrasiloxane (D4), and the cyclic hydrogen siloxane is 1,3,5,7-tetramethylcyclotetrasiloxane (D4h).

9. The method of claim 7, wherein the disiloxane is 1,3-bis[3-(2-hydroxyethoxy)propyl]tetramethyl disiloxane or 1,3-bis[hydroxybutyl]tetramethyl disiloxane.

10. The method of claim 7, wherein the amide-containing hydrophilic monomer is selected from the group of amides comprising N-vinyl pyrrolidone, N-allyl pyrrolidone, N-vinyl-N-methyl acetamide and a combination thereof; and the phosphorylcholine-containing hydrophilic monomer is 2-methacryloyloxyethyl phosphorylcholine (MPC).

11. The method of claim 7, wherein the rhodium-based catalyst is tris(dibutylsulfide) rhodium trichloride.

12. The method of claim 7, wherein the diisocyanate is isophorne diisocyanate (IPDI), toluene-2,4-diisocyanate, or toluene-2,6-diisocyanate.

13. The method of claim 7, wherein the ethylenically unsaturated monomer containing electrophiles is selected from the group of amides comprising isocyanatoethyl methacrylate, methacryloyl chloride and methacrylic anhydride; and the ethylenically unsaturated monomer containing nucleophiles is 2-hydroxyethyl methacrylate (HEMA).

* * * * *